(12) United States Patent
Foster et al.

(10) Patent No.: US 8,993,311 B2
(45) Date of Patent: *Mar. 31, 2015

(54) MULTI-STAGE CARTRIDGE FOR MEMS PARTICLE STORING SYSTEM

(75) Inventors: John S. Foster, Santa Barbara, CA (US); Daryl W. Grummitt, Santa Barbara, CA (US); John C. Harley, Santa Barbara, CA (US); James P. Linton, San Diego, CA (US); Jaquelin K. Spong, Falls Church, VA (US); Douglas L. Thompson, Goleta, CA (US)

(73) Assignee: Innovative Micro Technology, Goleta, CA (US)

( * ) Notice: Subject to any disclaimer, the term of this patent is extended or adjusted under 35 U.S.C. 154(b) by 347 days.

This patent is subject to a terminal disclaimer.

(21) Appl. No.: 13/506,892

(22) Filed: May 23, 2012

(65) Prior Publication Data

US 2012/0255373 A1 Oct. 11, 2012

Related U.S. Application Data

(63) Continuation-in-part of application No. 13/374,899, filed on Jan. 23, 2012, now Pat. No. 8,822,207.

(60) Provisional application No. 61/457,169, filed on Jan. 21, 2011.

(51) Int. Cl.

| | | |
|---|---|---|
| *C12M 1/36* | (2006.01) | |
| *C12M 1/38* | (2006.01) | |
| *C12M 3/00* | (2006.01) | |
| *C12M 1/00* | (2006.01) | |
| *B01L 3/00* | (2006.01) | |
| *B01L 7/00* | (2006.01) | |
| *G01N 15/10* | (2006.01) | |
| *G01N 15/14* | (2006.01) | |

(52) U.S. Cl.
CPC .......... *C12M 47/04* (2013.01); *B01L 3/502761* (2013.01); *B01L 7/52* (2013.01); *B01L 2200/0652* (2013.01); *B01L 2300/0816* (2013.01); *B01L 2400/043* (2013.01); *B01L 2400/0439* (2013.01); *B01L 2400/0478* (2013.01); *G01N 2015/1081* (2013.01); *G01N 2015/149* (2013.01)
USPC .................. 435/288.5; 435/288.7; 435/288.3; 435/288.4; 435/305.1; 435/305.2

(58) Field of Classification Search
CPC .................... B01L 3/502738; B01L 3/502761; B01L 2200/0652; B01L 2400/043; B01L 2400/0633
USPC .......... 435/288.7, 288.3, 288.4, 288.5, 305.1, 435/305.2
See application file for complete search history.

(56) References Cited

U.S. PATENT DOCUMENTS

| | | |
|---|---|---|
| 6,838,056 B2 | 1/2005 | Foster |
| 7,220,594 B2 | 5/2007 | Foster et al. |

(Continued)

*Primary Examiner* — Nathan Bowers
(74) *Attorney, Agent, or Firm* — Jaquelin K. Spong

(57) ABSTRACT

A disposable cartridge is described which is equipped with a plurality of microfabricated particle sorting structures. The disposable cartridge may include passageways which connect fluid reservoirs in the cartridge with corresponding microfluidic passageways on the particle sorting structure. A flexible gasket may prevent leakages and allow the fluid to cross the gasket barrier through a plurality of holes in the gasket, allowing fluid to be transferred from the reservoirs to the microfabricated particle sorting structures. The plurality of particle sorting structures may be arranged in the disposable cartridge in order to perform multiple separation operations, such as a sequential or parallel sorting operation.

18 Claims, 13 Drawing Sheets

(56) References Cited

U.S. PATENT DOCUMENTS

| | | |
|---|---|---|
| 7,229,838 B2 | 6/2007 | Foster et al. |
| 7,264,972 B2 | 9/2007 | Foster |
| 2007/0178529 A1* | 8/2007 | Breidford et al. .............. 435/7.1 |
| 2008/0050283 A1* | 2/2008 | Chou et al. .................... 422/101 |
| 2012/0009619 A1* | 1/2012 | Gilbert et al. ................... 435/29 |

* cited by examiner

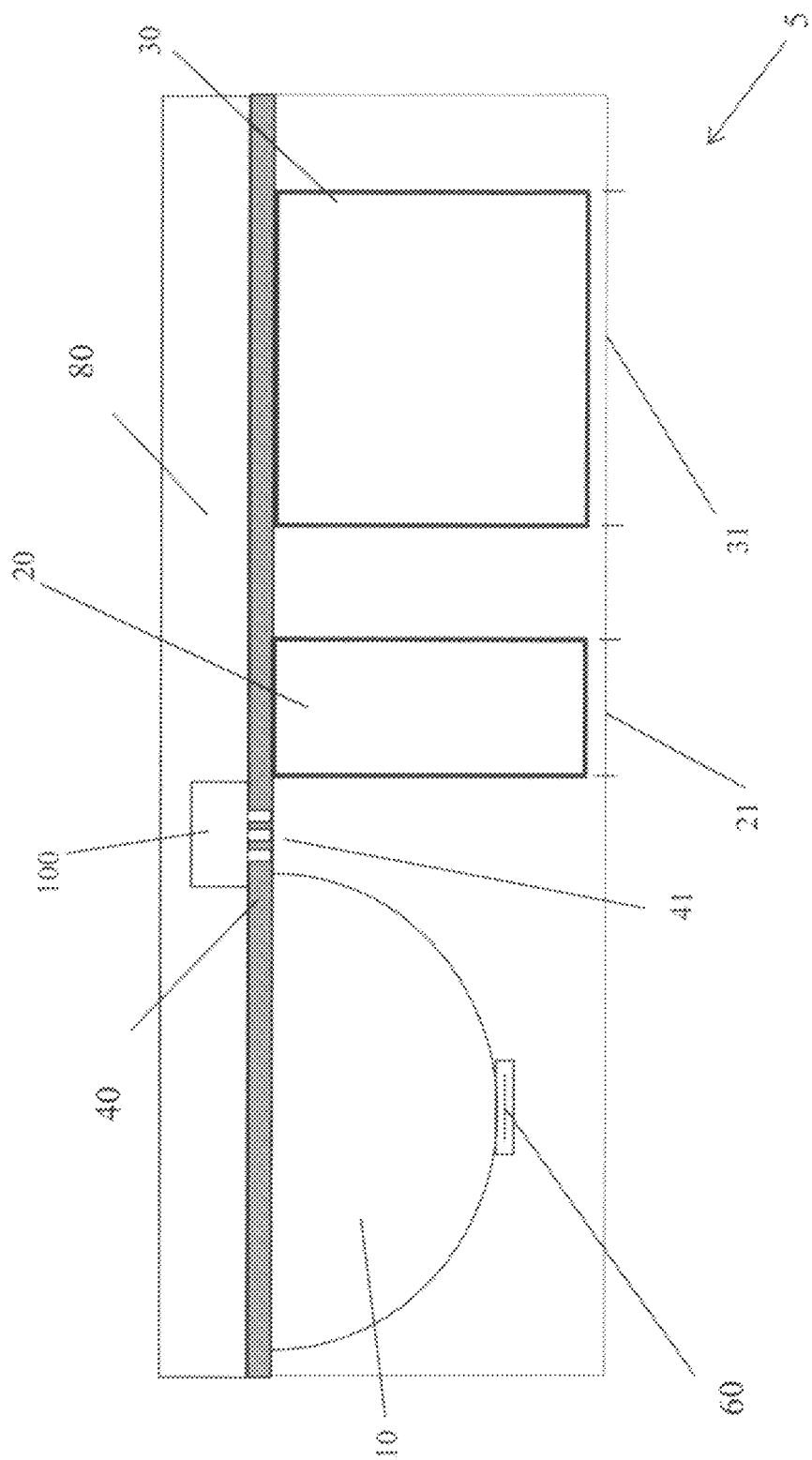

MULTI-STAGE CARTRIDGE FOR MEMS PARTICLE STORING SYSTEM

CROSS REFERENCE TO RELATED APPLICATIONS

This application is a continuation-in-part and claims priority to U.S. patent application Ser. No. 13/374,899, filed Jan. 23, 2012, which is based on U.S. Provisional Patent Application Ser. No. 61/457,169, filed Jan. 21, 2011, and incorporated by reference herein in its entirety. This application is also related to U.S. patent application Ser. No. 13/374,898, also filed on Jan. 23, 2012, and incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

This invention relates to a system and method for sorting small particles in a fluid stream with a MEMS device.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example.

MEMS devices, in the form of a movable valve, may be used as a sorting mechanism for sorting various particles, such as cells from a fluid stream such as blood. The particles may be transported to the sorting device within the fluid stream enclosed in a microchannel, which flows under pressure. Upon reaching the MEMS sorting device, the sorting device directs the particles of interest to a separate receptacle, and directs the remainder of the fluid stream to a waste receptacle.

A number of patents have been granted which are directed to such MEMS-based particle sorting devices. For example, U.S. Pat. No. 6,838,056 (the '056 patent) is directed to a MEMS-based cell sorting device, U.S. Pat. No. 7,264,972 b1 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Each of these patents is hereby incorporated by reference, and each is assigned to Innovative Micro Technology, assignee of the present invention.

MEMS-based cell sorter systems may have substantial advantages over existing fluorescence-activated cell sorting systems (FACS) known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between sample, inability to sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

SUMMARY

A system and method are described for separating particles of interest from the remainder of a fluid stream using a MEMS device. The system may make use of a unique micromechanical MEMS actuator which may improve the speed, simplicity and manufacturability of the particle sorting system. The MEMS actuator may be housed in a unique, disposable, self-contained cartridge which also houses a sample reservoir, a sorted reservoir, and waste reservoir, as well as the fluidic pathways between these reservoirs.

A particle sorting system based on this cartridge and MEMS actuator is described. In contrast to existing FACS flow cytometers, the MEMS-based cell sorter does not rely on a sheath fluid, and does not atomize the droplets containing the target cells. As a result, the MEMS-based cell sorting system can sort rare cells such as cancer cells or tumor cells, sperm cells, or other particles with outstanding speed and precision, and a very high proportion of the cells (>95%) are viable after sorting. The system is small, inexpensive and requires virtually no sterilization as the components in contact with the sample fluid are discarded after use.

The disposable cartridge may include at least one microfabricated particle sorting structure formed on a substrate and installed in the substantially sealed, disposable cartridge, a quantity of biocompatible material with a plurality of fluid reservoirs disposed therein, with one or more fluidic passageways formed between the microfabricated particle sorting structure and the reservoirs, and a flexible gasket covering the reservoirs, wherein a plurality of holes formed in the gasket allows a fluid flow to between at least one of the reservoirs and the microfabricated particle sorting structure.

A system and method are described for separating particles of interest from the remainder of a fluid stream. The system may make use of a unique micromechanical actuator in the aforementioned disposable cartridge. The disposable cartridge improves the speed, simplicity, cost and manufacturability of the particle sorting system, and completely encloses the sample stream. Because the cartridge is discarded between samples, no re-sterilization of the system is required.

These and other features and advantages are described in, or are apparent from, the following detailed description.

BRIEF DESCRIPTION OF THE DRAWINGS

Various exemplary details are described with reference to the following figures, wherein:

FIG. 3 is simplified cross sectional view of the cartridge shown schematically in FIG. 2, showing the flexible gasket;

DETAILED DESCRIPTION

The system described herein is a MEMS based particle sorting system which may make use of a unique, self-contained disposable cartridge which houses a MEMS chip and actuator on board the cartridge. The MEMS actuator design may improve the speed, precision, cost and manufacturability of the system, compared to prior art systems, and is further described in co-pending U.S. patent application Ser. No. 13/374,898, filed on Jan. 23, 2012 and incorporated by reference in its entirety. Use of the disposable, self-contained cartridge allows the system to remain uncontaminated by the sample fluid, and thus no sterilization of the system is needed. These features enable an inexpensive high performance cell sorting system, designed around the MEMS actuator and disposable cartridge, which includes a detector, a force-generating apparatus, and various optical inspection equipment on board in the system.

In the figures discussed below, similar reference numbers are intended to refer to similar structures, and the structures are illustrated at various levels of detail to give a clear view of the important features of this novel device.

Figure 1:
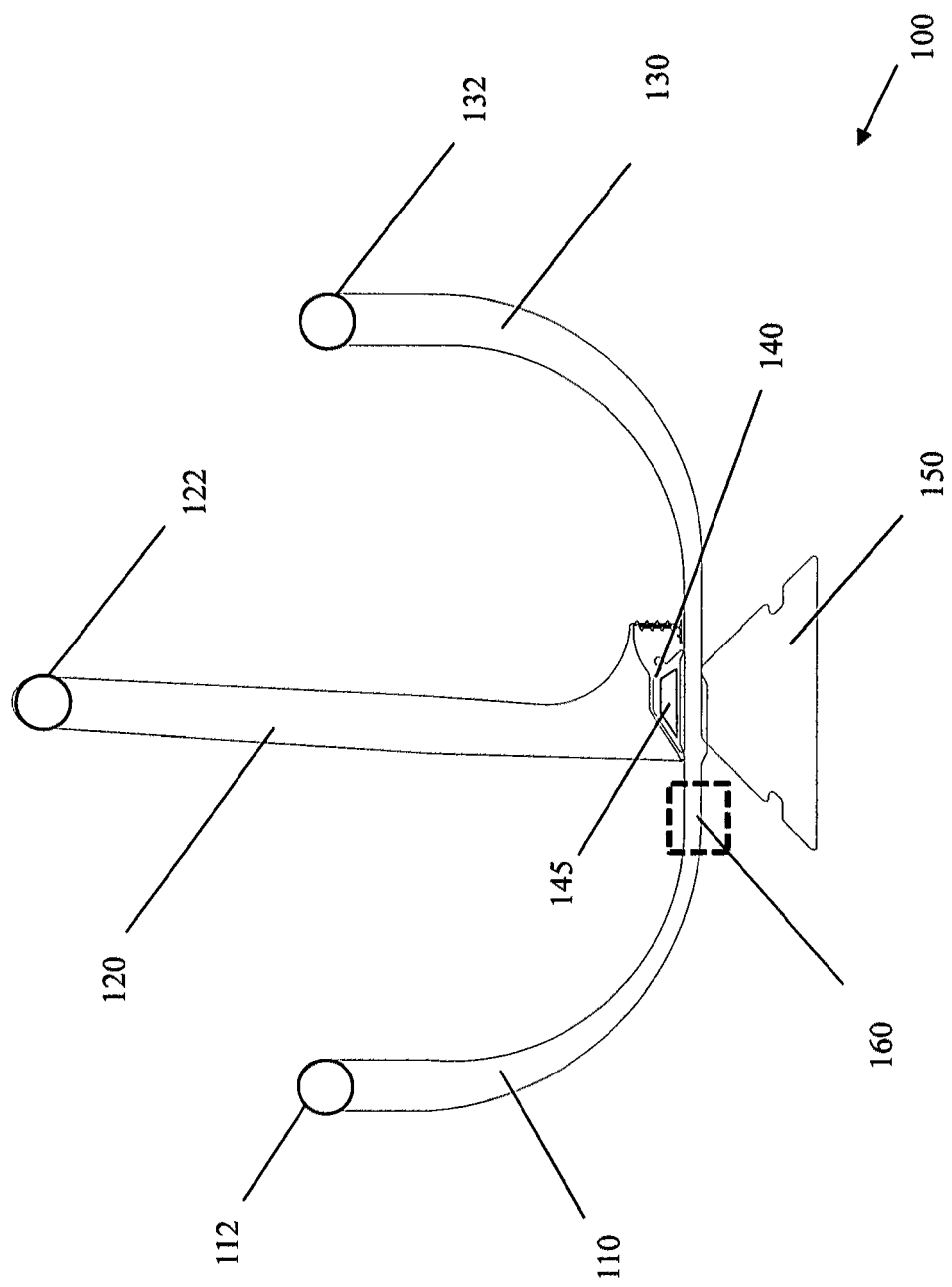
FIG. 1 is a simplified illustration of the MEMS actuator in the MEMS particle sorting system.

FIG. 1 is a schematic illustration of the MEMS particle sorting actuator, which is usable in the MEMS particle sorting system described below. The area designated 100 refers to a portion of a semiconductor substrate that includes a microfabricated device, that is, area 100 is a semiconductor chip containing the microfabricated sorting mechanism. The substrate or chip 100 also defines a plane in which the microdevice is fabricated, as well as the plane in which the microdevice moves. The motion and fabrication plane is generally parallel to the surface of the substrate 100, and in the plane of the paper.

The substrate or chip 100 may also include a plurality of small fluidic channels 110, 120 and 130 formed in the substrate 100. The fluidic channels allow a fluid sample stream to flow therein, wherein the fluid stream may contain a multitude of particles, some of which are to be separated from the others, forming a purified sample at the output. The channels may include an input channel 110 which admits the sample fluid from an input via hole 112 in substrate 100, a sort channel 120 which directs the sorted target particles into sort output via hole 122 and on to sort reservoir 20 contained in the cartridge (see FIG. 3), and a waste channel 130 which allows all the non-target particles to flow through the device to be routed through a waste via hole or port 132 to be collected in a waste reservoir 30, also contained in the cartridge (See FIG. 3). Examples of target particles may include stem cells, cancer cells, bacteria, blood cells, sperm cells, lymphocytes, T-cells, for example. The fluid stream may be blood, lymph, semen, saline or dilute samples of these fluids, for example. The substrate or chip 100 may be covered by an optically transparent, flat layer which encloses the fluidic channels 110, 120 and 130, while allowing light to pass through this layer.

While in the fluid stream, the components of the sample may pass through a detection region 160, and past the movable structure 140 of the MEMS actuator, which either diverts the stream into the sort channel 120 and to port 122, or allows it to pass to the waste channel 130 and port 132. The chip 100 may include areas 145 and 150 in the MEMS actuator into which a magnetically permeable material has been inlaid, whose function is described more fully below.

In the detection region 160, the target particle may be distinguished from the other constituents of the fluid sample. The detection means may be, but is not necessarily, a microfabricated structure located in the input channel 120 upstream of the movable structure 140, and generally in detection region 160. The detection means may be based on any number of characteristics or attributes that distinguish the target particle from the others in the fluid stream. For example, the particles may be distinguished by, for example, differences in an electrical attribute, a hydrodynamic attribute, a magnetic attribute, an optical attribute, a thermal attribute, mass, and a mechanical attribute of the particle, to name just a few. This list is not meant to be exhaustive, but instead to provide examples of detection systems which may be used with the actuator described herein.

In one embodiment, the target particle may be a particular cell which may be tagged with a fluorescent tag, which emits light of a particular color when irradiated by a laser at a particular wavelength. Such tags are well known in the field and include for example fluorescein, Texas Red, phycobiliproteins, cyanine derivatives and rhodamine. While much of this disclosure is directed to this application, it should be understood that the systems and methods described herein are also applicable to other detection mechanisms used to distinguish particles one from another. These mechanisms may be well known, or may yet be invented.

Upon passing through the detection region 160, a signal is generated by the detector (not shown) indicating that a target particle is present in the detection region 160. After a known delay, a signal is generated by a controller which indicates that the sorting gate, i.e. the movable structure 140, is to be opened, in order to separate the target particle which was detected, from the other components in the fluid stream. Both the flap-like movable structure 140 and the fixed feature 150 may comprise permeable magnetic materials, so that a magnetic force may arise between them when a magnetic field is present. When the signal is generated by the controller, a force is generated between the embedded magnetically permeable material 145 in the flap-like movable structure 140 and a fixed feature 150, which draws the flap-like movable structure 140 towards the fixed feature 150. This motion closes off waste channel 130 and waste port 132, and redirects the target particle into a sort channel 120 and sort port 122 at the end of sort channel 120. The sorted sample is subsequently collected from a sort reservoir in the disposable cartridge which holds the sorted sample.

In particular, the signal generated by the detector indicates that a force-generating mechanism is to be activated. This force-generating mechanism may be a current-carrying coil and a permeable magnetic core, which resides in the cell sorting system and is more fully described with respect to FIG. 5, below. Accordingly, the force-generating structure is a separate mechanism that is not directly, mechanically coupled to the movable structure 140, the MEMS actuator 100 or the disposable cartridge 5. Upon receiving the signal that the target particle has been detected, a current may be applied to the coil, generating a magnetic field in the permeable core. This field is shaped by the fixed feature 150 in order to provide a region with a high density of flux lines in the vicinity of the fixed feature 150. As is well known from elementary magnetostatics, the permeability portion 145 of movable structure 140 may be drawn toward regions of increasing flux density, and therefore may be drawn toward fixed feature 150, closing the waste channel 130 and opening the sort channel 120. The details of this sorting mechanism are described in greater detail in co-pending U.S. patent application Ser. No. 13/374,898, filed on an Jan. 23, 2012 and incorporated by reference in its entirety.

Figure 2:
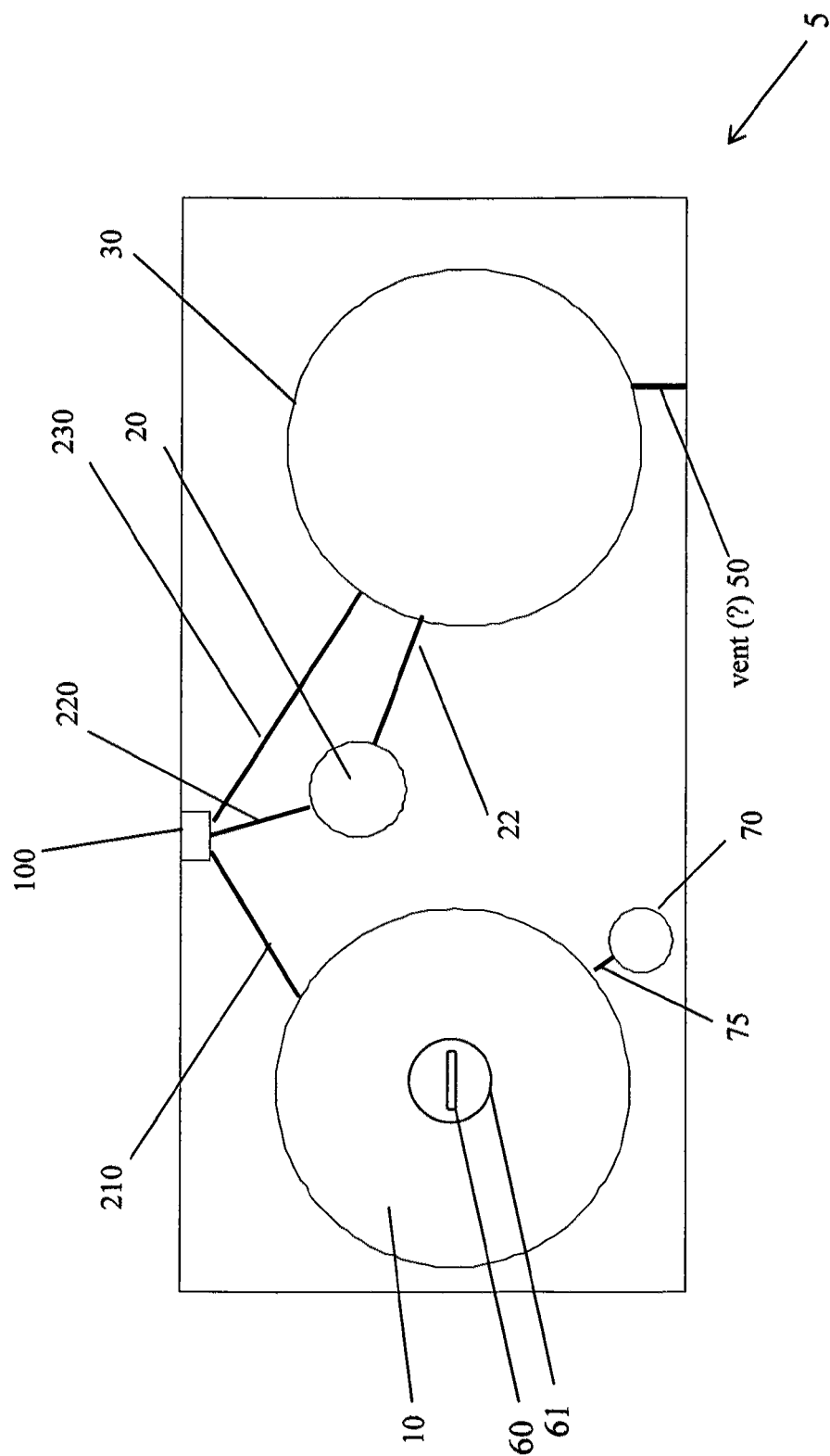
FIG. 2 is a simplified plan view of a first embodiment of the MEMS actuator disposed in the disposable cartridge.

FIG. 2 is a simplified illustration of the MEMS actuator chip 100 disposed in the disposable cartridge 5. The cartridge may be made of a quantity of a biocompatible material such as polycarbonate or poly methyl methacrylate (PMMA), or even metal. Preferably, this material is also sterilizable and moldable. The cartridge body may be machined, or injection molded from the biocompatible material, for example. Preferably, this quantity of biocompatible material may be transparent, allowing the position of the MEMS chip 100, as well as the sample reservoirs 10, 20 and 30 to be viewed from outside the cartridge 5.

As mentioned above, the cartridge material may be optically transparent, allowing viewing of both the MEMS chip 100 from above, and the fluid reservoirs from below. The ability to view the MEMS chip 100 may enable better alignment of the cartridge with respect to the detection system and force-generating mechanism, both of which may reside in the cell sorting system shown in FIG. 5. The word "cartridge" should be understood to mean a container holding a quantity of fluid and designed for insertion into a mechanism, in this case, the MEMS particle sorting system. The cartridge is hereafter described as "self-contained," which should be understood to mean that the cartridge may be handled as a complete unit, it may be inserted or withdrawn from the particle sorting system in its entirety, and that the sample fluid, sorted fluid and waste fluid are completely contained within the cartridge at all times. "Substantially sealed" should be understood to mean that once the fluids are introduced to the cartridge, the fluid flows entirely within the cartridge, although one or more vents in the fluid reservoirs may allow gas exchange with the external environment. "Disposable" should be understood to mean that the cartridge may be easily withdrawn from the particle sorting system, and replaced with another like cartridge. After use, the disposable cartridge may be discarded, or it may be used to store the sample for a longer period of time, for example, in a freezer. This becomes a significant cost advantage in terms of the cost of the cartridge and the cost of operation of the particle sorting system, described further below, because the more expensive components may reside in the cell sorting system and be reused.

The cartridge 5 may have reservoirs for sample 10, waste 30 and the sorted effluent 20. Each of the reservoirs may be connected to the MEMS chip 100 by a small passageway 210, 220 and 230 in the plastic of the cartridge, and is connected to the corresponding microfluidic channels 110, 120 and 130 in the chip 100. For example, passageway 220 may connect sort reservoir 20 with the sort channel 120 in MEMS chip 100 by way of via hole 122 in substrate 100. Passageway 230 may connect waste reservoir 30 with the waste channel 130 in MEMS chip 100. Passageway 210 may connect input sample reservoir 10 with the input channel 110 in MEMS chip 100. The actual connection between these passageways may be accomplished by a flexible gasket, as described further below.

As mentioned above, the disposable cartridge 5 may be equipped with a flexible gasket. This gasket may have several functions: it may provide a fluid seal to the passageways; it may also allow the fluid to traverse the gasket through a set of holes in the gasket; and it may provide a flexible membrane for applying pressure to the input reservoir and causing the fluid sample to flow. This pressurization method is described in greater detail below with respect to FIGS. 4*a* and 4*b* below.

The cartridge 5 may also be equipped with a flexible fill septum 70 which allows the sample fluid to be introduced to the sample reservoir 10 with a hypodermic needle into the septum, for example. In particular, a hypodermic needle may be inserted into the septum 70, the plunger depressed, and fluid from the hypodermic chamber is forced into the sorting reservoir 10 through a narrow passage 75 in the plastic. This may prevent the sample fluid from exiting the input sample reservoir via this route when under pressurization, rather than through passageway 210.

The input reservoir may also be equipped with a magnetic stir bar 60 which may be confined in a depression or chamber 61 formed with the input reservoir 10. The magnet 60 may interact with a rotating magnetic field in the cell sorting system described below, in order to agitate or mix the components of the fluid sample, or to maintain the components in suspension.

The cartridge 5 may also be equipped with a vent 50 which allows gas to escape from the waste reservoir 30 as it is displaced by fluid pumped from the input reservoir 10. This vent may reduce the pressure required on the input reservoir 10 in order to cause the sample fluid to be completely transferred from the input reservoir 10, through the MEMS chip 100, and into either the sort reservoir 20 or the waste reservoir 30. The vent 50 may also contain a micropore filter (not shown), which creates a barrier to particles or bacteria entering the cartridge 5, and may thus help maintain the sterility of the cartridge 5. A vent 22 may also be used to connect reservoir 20 and reservoir 30, to reduce the pressure in reservoir 20. This vent 22 may include a filter such that cells or other particles of interest cannot pass between reservoirs 20 and 30. Alternatively, vent 22 can be routed directly out of the disposable cartridge in like manner as vent 50.

FIG. 3 is a cross sectional diagram of the disposable cartridge 5 showing the flexible gasket 40, a plurality of gasket through holes 41, along with the profiles of the input reservoir 10, sort reservoir 20 and waste reservoir 30. The gasket 40 may provide a fluid seal to the passageways 110, 120 and 130, and may include a plurality of channels 41 through which the fluid in passageways 210, 220 and 230 reach the MEMS chip 100 and microfluidic channels 110, 120 and 130 by way of via holes 112, 122 and 132 in substrate 100. The flexible gasket may also form a flexible membrane over the input reservoir, allowing a piston applied thereto to force the fluid from the input reservoir to through passageway 210 and to MEMS chip 100, and to movable sorting structure 140 via input channel 110. The gasket may be formed of a biocompatible, flexible material such as silicone, which may be stamped or molded into the desired outline. The gasket may be less than about 500 microns thick, in order to provide a sufficiently flexible yet robust membrane.

A clear, plastic lid 80 may secure the MEMS chip 100 in the disposable cartridge 5, and may secure the flexible gasket 40 to the cartridge base. The plastic lid 80 may simply be glued or cemented to the flexible gasket 40, after alignment of the plurality of through holes 41 to the plurality of passageways 110, 120 and 130. Using a clear material for the cartridge lid 80 allows the condition of the MEMS chip 100 to be seen from above, so as to align the position of the MEMS chip 100, or the MEMS chip 100 may be viewed through the clear base material. This may allow alignment of the movable structure 140 and detection region 160 with respect to the detector and force-generating apparatus.

Another important feature of the disposable cartridge 5 is the cross sectional profile of the input reservoir 10, the sorted reservoir 20 and the waste reservoir 30, as shown in FIG. 3. The input reservoir 10 may have a curved or hemispherical floor as shown, whereas the sort reservoir 20 and waste reservoir 30 may have rectangular cross sectional profiles. The curved or hemispherical spherical profile of the input reservoir may make it consistent with the piston fluidic drive, as explained in greater detail with respect to FIGS. 4a and 4b below. The rectangular profile of the sort reservoir 20 and waste reservoir 30 may have a flat floor, which allows their contents to be viewed from below. This capability may be convenient for assessing the quality and condition of the sort effluent and waste effluent. One viewing area 21 may be provided for the sort reservoir 20, and another viewing area may be provided for the waste reservoir. For cartridge designs which do not use optically transparent materials, these viewing areas may be optically transparent windows in the opaque cartridge materials which may be uncovered when viewed, and otherwise covered with an opaque shutter or other covering.

In particular, an optical imaging system may be placed beneath the disposable cartridge 5, either when the cartridge is in the cell sorting system or when it has been withdrawn. When withdrawn, the disposable cartridge 5 may simply be placed on a microscope stage and the contents of the sort reservoir 20 and waste reservoir 30 may be imaged and inspected. This may be a valuable feature in obtaining a rough estimate of the effectiveness or success of a particular sorting run. The contents of the reservoirs need not be withdrawn to allow this inspection.

Figure 4A:
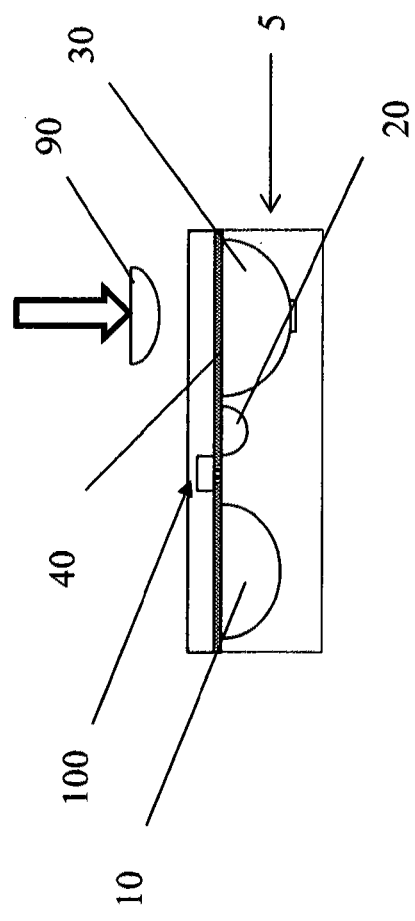
FIGS. 4a and 4b are schematic views of one embodiment of a pumping mechanism for forcing fluid through the disposable cartridge and MEMS actuator.
Figure 4B:
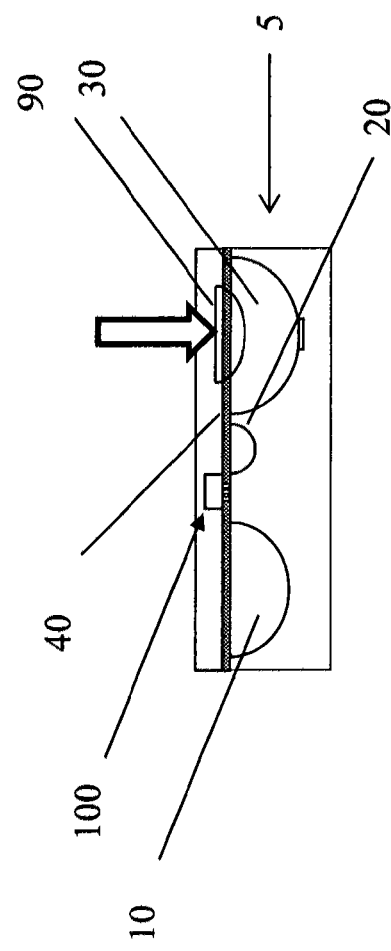

FIGS. 4a and 4b are a schematic illustration of the propulsion system which may be used to force the sample fluid through the input passageway 210 and channel 110 to the MEMS chip 100 and then out through the sort channel 120 to sort reservoir 20 (if a target particle) or waste channel 130 and waste reservoir 30 (if another component). The propulsion system may include a shaped piston or plunger 90, which has approximately the same contour as the input sample reservoir 10. For example, if the input sample reservoir has a spherical shape, the piston or plunger 90 may have a similar spherical shape of smaller radius. This allows the piston or plunger to deflect the flexible gasket 40 onto the surface of the fluid pool in the input reservoir, creating a pumping pressure which forces the fluid through the input passageway 210 to the input channel 110, to the detection region 160, past the movable structure 140 and into either the sort channel 120, sort passageway 220 and sort reservoir 20, or the waste channel 130, waste passageway 230 and waste reservoir. From the sort reservoir 20, the sorted sample may be retrieved by a hypodermic needle through another septum, or otherwise unloaded from the disposable cartridge 5 for further processing or analysis.

In other embodiments, the pressure against the membrane or gasket may be applied by providing baric pressure in a pressure chamber, rather than by a plunger or piston 90.

FIG. 4a shows the disposable cartridge in relation to the piston 90 before the pressure is applied from the piston 90 to the gasket 40. This may be the position of the piston 90 during the loading or unloading of the cartridge 5 into the cell sorting system, which is described below with respect to FIG. 5, which shows the complete system. In FIG. 4b, the piston 90 is lowered into contact with the flexible gasket 40, applying a pressure to the surface of the fluid. This pressure forces the fluid through the input passageway 110, through the MEMS chip 100, and then to the sort reservoir 20 or the waste reservoir 30.

Figure 5:
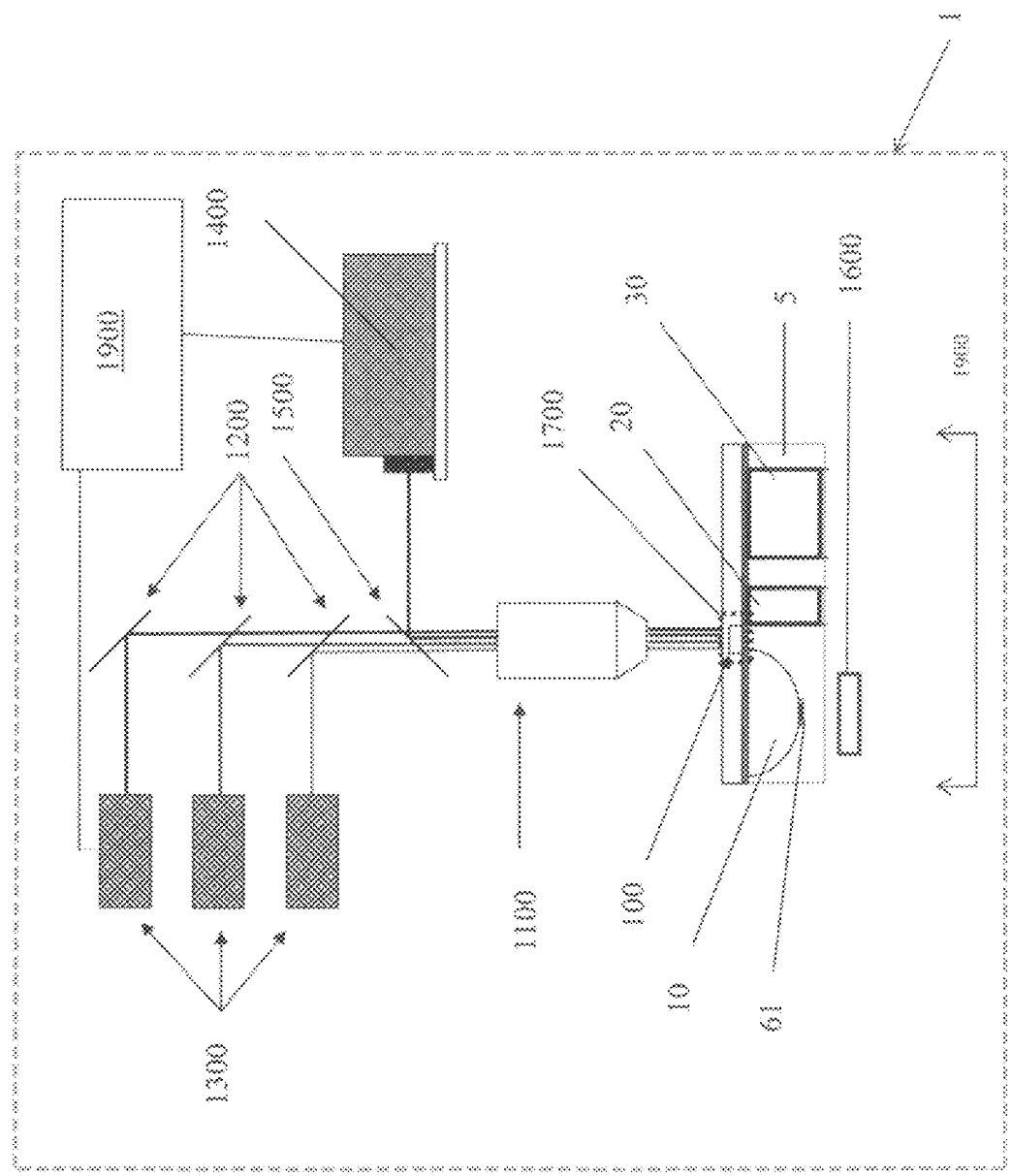
FIG. 5 is a schematic view of the disposable cartridge and MEMS actuator in a particle sorting system with an optical detectors for detecting tagged particles.

FIG. 5 is a more detailed illustration of one embodiment of a particle sorting system 1 using the microfabricated flap valve movable structure 140 and MEMS chip 100 in the disposable cartridge 5. Reference number 5 refers to the disposable, self-contained cartridge 5 described above that houses a sample reservoir 10, a sort reservoir 20 and waste reservoir 30, which are in fluid communication with input channel 110, sort channel 120 and waste channel 130 shown in FIG. 1. The MEMS chip 100 containing the MEMS actuator 140 may be disposed in the front of this cartridge 5 as shown in FIG. 3. This cartridge 5 may be disposed in the system such that a laser and detector are situated directly adjacent to and above the detection region 160 shown in FIGS. 1 and 2.

In one embodiment, the target particle may be a particular cell, such as a stem cell, or a cancer cell, which has been tagged with a fluorescent marker. This marker emits photons having a particular energy when irradiated with a laser operating at a predefined wavelength. Accordingly, in this cell sorting system, a laser source 1400 may be directed by a turning mirror 1500 through the detection optics 1100 onto the MEMS chip 100 in the detection region 160 shown in FIG. 1. The optical axis of the detection optics 1100 and the laser source 1400 may be collinear, at least over a portion of the optical path. Thus, the orientation of the laser application and optical detection along this optical axis may be perpendicular or orthogonal to the substrate fabrication plane, orthogonal to the plane of motion of the sorter flap movable structure 140 and orthogonal to the flow of the sample fluid through the detection region. This may have important consequences as the light traverses the surfaces with an orthogonal angle of incidence, which may reduce specular reflection and thus reduce or eliminate a noise source in the detection scheme.

The fluorescence emitted from the irradiated particles may be shaped by detection optics 1100 and separated by dichroic mirrors 1200 and directed into a bank of photodetectors 1300. A plurality of photodetectors may accommodate multiple wavelengths of emitted light, for multiparametric detection. The signal output by the photodetectors 1300 indicates the presence or absence of the target particle in the detection region 160. The signal may be delivered to a controller 1900, which manages the relative timing of the components in the particle sorting system 1, and collects the data. The controller 1900 may be a general purpose computer or a specialized circuit or ASIC. Upon detection of the target particle, a signal is generated by the controller 1900 which energizes the force-generating or flux-generating apparatus 1700. The force generating apparatus is a device which causes a force to arise in the movable structure itself, causing the motion of the movable structure toward the force-generating apparatus, which has an equal and opposite force arise therein. In general, this force-generating apparatus is not directly mechanically coupled to the movable structure 140. For example, the force-generating apparatus 1700 may be a source of magnetic flux which causes a magnetostatic force to arise in the permeable material 145 of the movable structure. This force pulls the flap or movable structure toward the force-generating apparatus 1700, opening the sort channel 120 and port 122 to the flow and closing the waste channel 130 and waste port 132. Importantly, the force-generating apparatus 1700 resides in the particle sorting system 1, rather than in the disposable cartridge 5. As mentioned previously, this may reduce the cost and complexity of the disposable cartridge 5.

As mentioned, in one embodiment, this force-generating apparatus 1700 is a source of magnetic flux, for example an electromagnet, which is energized to produce a magnetic flux from a current-carrying coil. The flap or movable structure 140 is also formed substantially from a permeable magnetic material, such as nickel-iron permalloy, which is drawn toward the gradient of this magnetic flux as is well known from elementary magnetostatics. This force pulls the flap or movable structure 140 toward the force-generating apparatus 1700, redirecting the target particle from the input channel 110 to the sort channel 120.

Shown only schematically because it is behind and obscured by the disposable cartridge 5 is the force-generating apparatus 1700, for example, a magnetic core with a wound coil. As mentioned previously, upon receiving the appropriate signal from one of more photodetectors 1300 indicating that a target particle is present in the detection region 160, a controller 1900 may energize the coil, producing a magnetic field which is shaped by the fixed features 150 in the vicinity of the movable structure 140. The permeable magnetic inlay 145 of the permeable structure is drawn toward the fixed feature 150, opening the sort channel 120 and closing the waste channel 130. By this means, the target particle is separated from the other components of the fluid stream and collected in the sort reservoir 20 in the disposable cartridge 5.

Also included in the cell sorting system 1 may be a mechanism which generates a rotating magnetic field 1600. This rotating field may simply be a rotating permanent magnet or a rotating coil. This rotating field may interact with bar magnetic stirrer 60, causing it to rotate in the magnet chamber 61, and mix the contents of the input reservoir 10 in which the magnet 60 is housed.

The disposable cartridge 5 may be inserted into a housing containing the components shown in FIG. 5. The insertion area may be a stage with mechanisms available for fine positioning of the disposable cartridge 5 against one or more data, which orient and position the detection region and movable structure 140 with respect to the collection optics 1100 and the force-generating apparatus 1700. If finer positioning is required, the input stage may also be a translation stage, which adjusts the positioning based on observation of the location of the movable structure 140 relative to the datum. This observation may be made through the optically transparent lid 80 or the quantity of transparent biocompatible material of the cartridge 5, as described above.

The MEMS cell sorting system 1 shown in FIG. 5 may also be equipped with a number of accessories. For example, accessory 1900 may be a vibration-generating mechanism, mechanically coupled to the disposable cartridge 5. This vibration-generating mechanism may be, for example, and ultrasound transducer, an audio speaker, a piezoelectric transducer, or the like, which is capable of applying a transitory pressure wave or acoustic vibration to the fluid in the disposable cartridge. This pressure wave or acoustic vibration may help in dispersing clots or coagulations, which are well known in association with biological and cellular materials. Adherent particles such as platelets and DNA fragments are often difficult to handle, especially given the small dimensions of the microfabricated particle sorting structure shown in FIG. 1. The vibration-generating mechanism may apply the acoustic power at any number of convenient points, for example, to the stage holding the disposable cartridge as shown in FIG. 5, or to the piston 90 in contact with the flexible gasket 40. Because of the modular architecture of the MEMS particle sorting system shown in FIG. 5, such accessories are relatively straightforward to implement.

In another embodiment, accessory 1900 may be a heating or refrigeration stage on which the disposable cartridge 5 is mounted. The heating or refrigeration stage may be thermally coupled to the disposable cartridge. It is well known that lowering the temperature of various biological materials may slow their metabolic processes, and thereby extend their lifetime and/or functionality. Spermatozoa are notoriously sensitive to temperature, for example. By using such a refrigeration stage, the sample fluid may be cooled throughout the sorting process, thereby increasing the viable proportion of the sorted effluent. Alternatively, applying heat to the disposable cartridge may speed up metabolic processes or catalyze other thermally activated processes. It should be understood that these accessories are optional and motivated by the requirements of the application, and are not required to practice this invention.

Cascade Material Begins Here

For any particle sorting mechanism, there is an inherent trade-off between sort purity and sort speed. One can only increase the fluid speed to a certain point, after which one runs into physical limitations of the sorter, for example, when the valve speed is such that there is insufficient time to open the valve or flap when a cell is detected. Beyond that limitation, the most obvious way to achieve more events per second is to increase the cell density. But, with increased cell density, the incidence of sort conflicts, wherein both a desired and an undesired cell are collected, also increases.

In order to overcome this limitation, a cell sample may theoretically be processed multiple times in a sequential sort strategy—initially a very rapid, crude sort followed by a—slower, high precision sort. This is generally not a practical option with a traditional FACS system as a result of massive cell dilution (from sheath fluid), slow processing speeds and unacceptable cell damage resulting from multiple passes through the high pressure electrostatic sorting mechanism. A single pass through a flow cytometer is exceptionally violent, with 10 m/sec velocities, explosive decompression from 60 psi to 0 psi. Cells are unlikely to survive such treatment on multiple passes without significant loss of viability. Even if one is willing to accept the dilution, manual processing and cell death, the yield losses on a FACS would be overwhelming. Also, the time constant per cycle for processing, cleaning, sterilization and certification is untenable and the sterility of the sample is completely compromised. As a result, this sequential sorting is not practical approach for FACS-based clinical cell sorting.

In contrast, for the disposable cartridge and particle sorting system described above, using the completely enclosed disposable cartridge described above, a multi-stage, "sequential" sort may be performed right on a single cartridge without intervening non-sterile cell manipulations and with negligible impact on cell viability. To implement this on a single cartridge there may be a plurality particle manipulation operations taking place in a single cartridge, for example, using a plurality of embedded MEMS sorting chips. In one embodiment, the plurality of MEMS sorting chips are separated by some extent, such that by shifting the cartridge body relative to the detector, the additional MEMS chips may become operational. This embodiment is described further below, and illustrated in FIGS. 6-10. More broadly, the disposable cartridge may include a secondary manipulation area upstream of the MEMS sorter, and this embodiment is described below with respect to FIG. 11.

Figure 6:
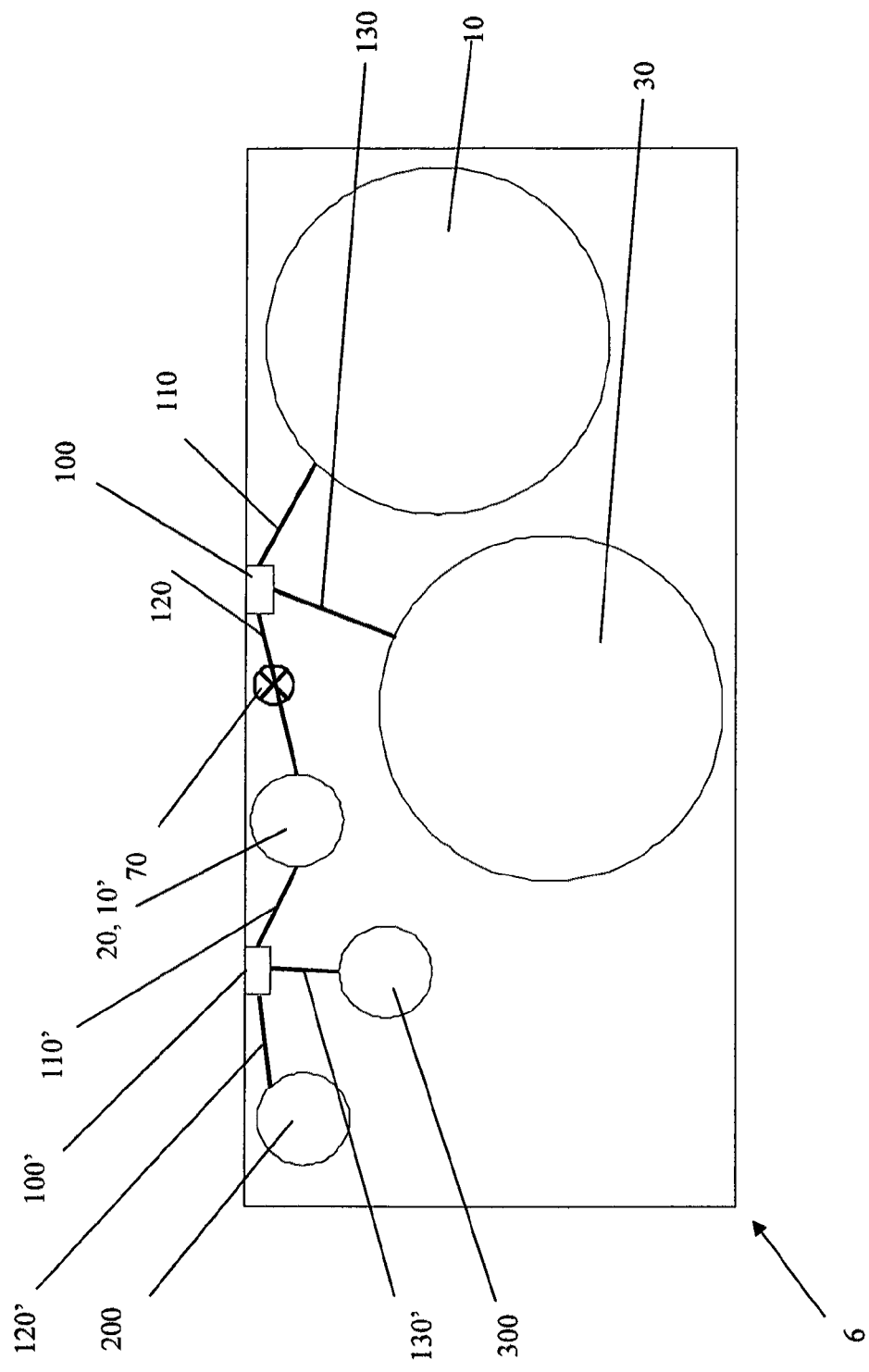
FIG. 6 is a schematic view of a MEMS particle sorting system using a disposable cartridge with a multiple separation stages.

Accordingly, a first sort may be run rapidly through a first sorting stage, to enrich target cells with negligible yield losses. The disposable cartridge is then shifted laterally within the detector and the sort output of the first sort now serves as the sample input for a sequential sorting stage, i.e. through a second or additional MEMS sorting chip at lower speeds and high precision gating. This process is analogous to fractional distillation in chemical plants. Using this approach, the sample remains sterile and non-manipulated through the entire sequential sorting process. An example of a cartridge adapted for sequential sorting is shown in FIG. 6. As seen in FIG. 6, the cartridge is adapted with a plurality of sorting stages, i.e. a plurality of MEMS chips rather than one. After the first sort, the cartridge is simply shifted laterally to bring the next MEMS chip into the interrogation region.

FIG. 6 is a simplified illustration of the MEMS actuator disposed in the sterile, disposable cartridge having multiple, in this case two, separation stages. This multistage cartridge 6 may be similar to disposable cartridge 5 in that the cartridge contains all of the sample fluid throughout the sorting process, and may simply be thrown away after sorting. A first separation stage 100 and a second separation stage 100' may be disposed in a serial arrangement, such that the sample fluid flows first through separation stage 100 for sorting, and the effluent is sorted again by separation stage 100'. Like disposable cartridge 5, disposable cartridge 6 may include a sample reservoir 10, a sort reservoir 20 and a waste reservoir 30. The sample, sort and waste reservoirs may be in fluid communication through a plurality of small passageways 110, 120 and 130 respectively, formed in the material of the cartridge, which in this embodiment is a biocompatible plastic. A valve 70 may allow or prevent the fluid from passing from MEMS chip 100 into sort reservoir 20. This valve may be used to prevent backflow from sort reservoir 20 back through MEMS chip 100 and input reservoir 10, when the sort reservoir is pressurized for the second stage of sorting through second MEMS chip 100'.

The first stage of sorting proceeds as described above, and a population or subset of target particles may be collected in sort reservoir 20. This sort may be done at relatively high speeds, in order to reduce the number of non-target particles present in the sample. Upon completion of this sort, the cartridge may be withdrawn and shifted laterally with respect to the optical system 1100, force-generating apparatus 1700 and pump mechanism 90. These mechanisms may now be positioned to act upon the second sorting stage 100'. For this second sort, the pump mechanism may act on the sort reservoir 20 rather than the input reservoir 10, the optical detection system 1100 may act on a new detection region in the second MEMS chip 100', and the force-generating apparatus 1700 may also act upon the second MEMS chip 100'. This sort may be done to achieve higher purity.

Alternatively, the detection parameters in the optical detection apparatus 1100 may be changed to select a different sub-population of target particles. As mentioned previously, the valve 70 may be activated to prevent backflow of the fluid to the first MEMS chip 100. The sorted effluent may be collected in the second sort chamber 200, with waste collected in the second waste chamber 300. As before, these reservoirs may be connected by small passageways in the biocompatible cartridge material.

Figure 7:
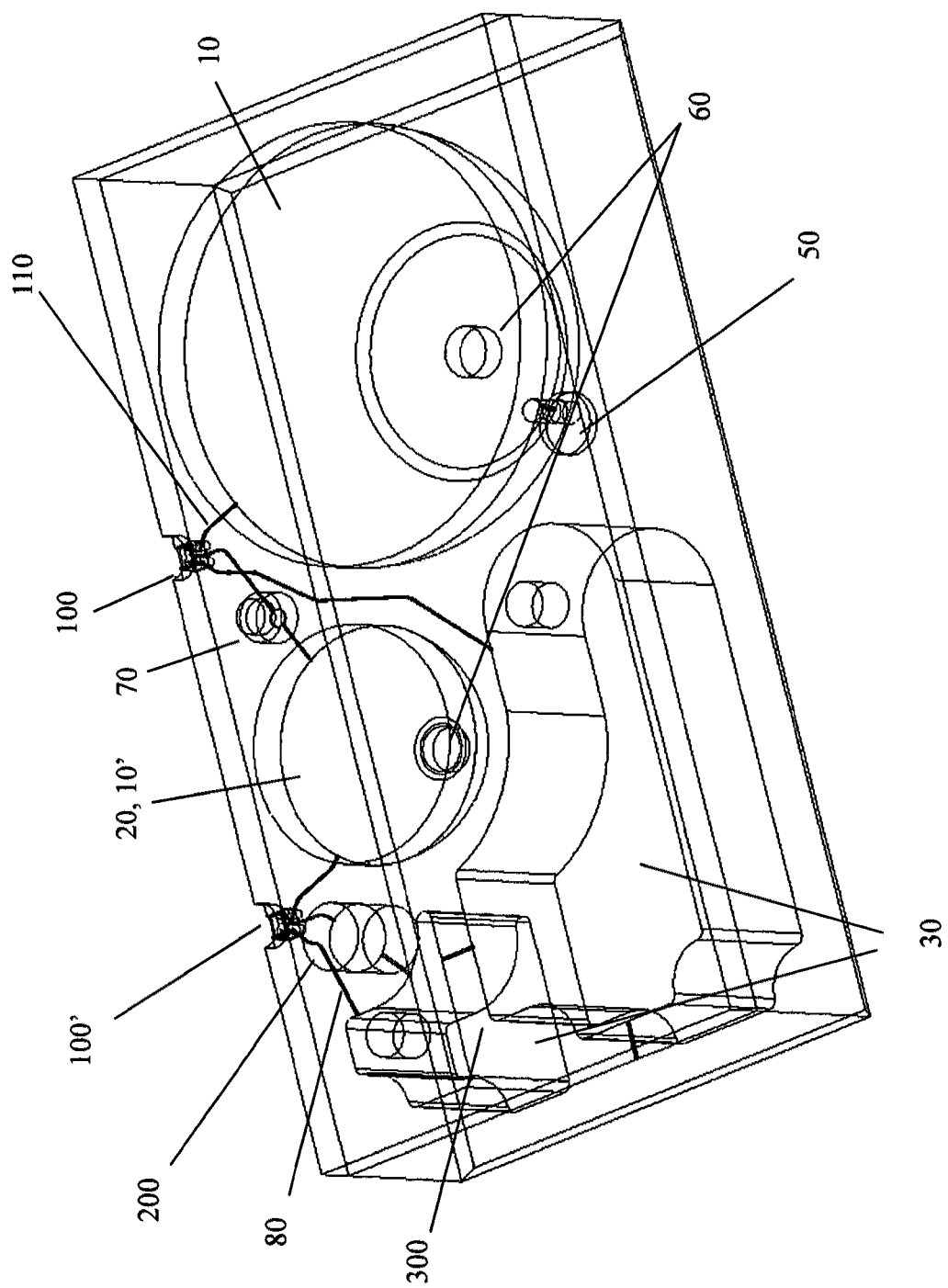
FIG. 7 is a more detailed computer-assisted design drawing of the two-stage sorting disposable cartridge of FIG. 3.

FIG. 7 is computer-assisted design rendering of the cartridge shown schematically in FIG. 6. This illustration shows the cartridge in greater detail, in perspective view. As described, the cartridge may include a first input reservoir 10, sort reservoir/second input reservoir 20/10', waste reservoir 30, second waste reservoir 300, and valve 70. Other structures may include vent/input septum 50, and stir bars 60, whose function is as described above with respect to disposable cartridge 5.

Figure 8:
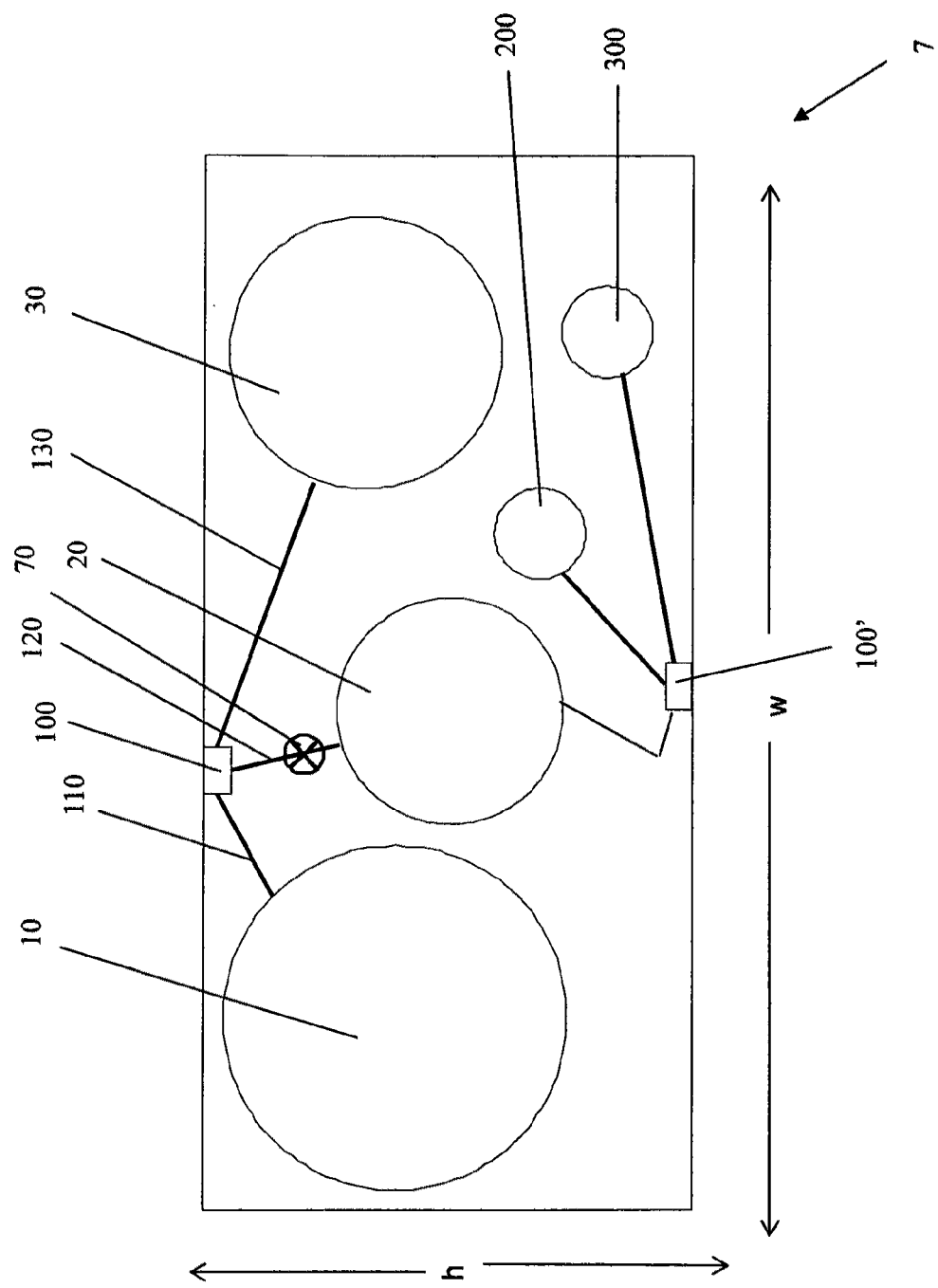
FIG. 8 is a schematic view of a second embodiment of a MEMS particle sorting system using a disposable cartridge with multiple sorting/separation stages.

As can be appreciated based on the foregoing descriptions, there may be a variety of ways to arrange the elements shown in FIG. 6. FIG. 8 is a simplified view of a second embodiment of the sterile, disposable cartridge 7 having multiple separation stages. In this embodiment, second separation stage 100' is disposed on the other face of the cartridge compared to first separation stage 100. The fluidic passageways may be re-arranged to accommodate this configuration. This configuration may be simpler to operate or implement, depending on the architecture and layout of the particle sorting system 1 in which it is intended to be used.

By using cartridge 6 or 7 with multiple separation stages, the input sample may first be roughly sorted, or "de-bulked" at high sort speed but relatively pure precision. This may generate a large volume of effluent, but the sample may not yet have the required purity. By sorting this sample times, the sort purity may achieve the desired levels.

This type of sequential sorting may be appropriate for samples having a large number of non-target cells. Bone marrow for example, which contains the valuable blood stem cells, also may include large numbers of non-target particles such as platelets, lymphocytes, and fragmentary DNA. These non-target particles may all need to be removed to acquire a population of blood stem cells having sufficient purity.

Figure 9:
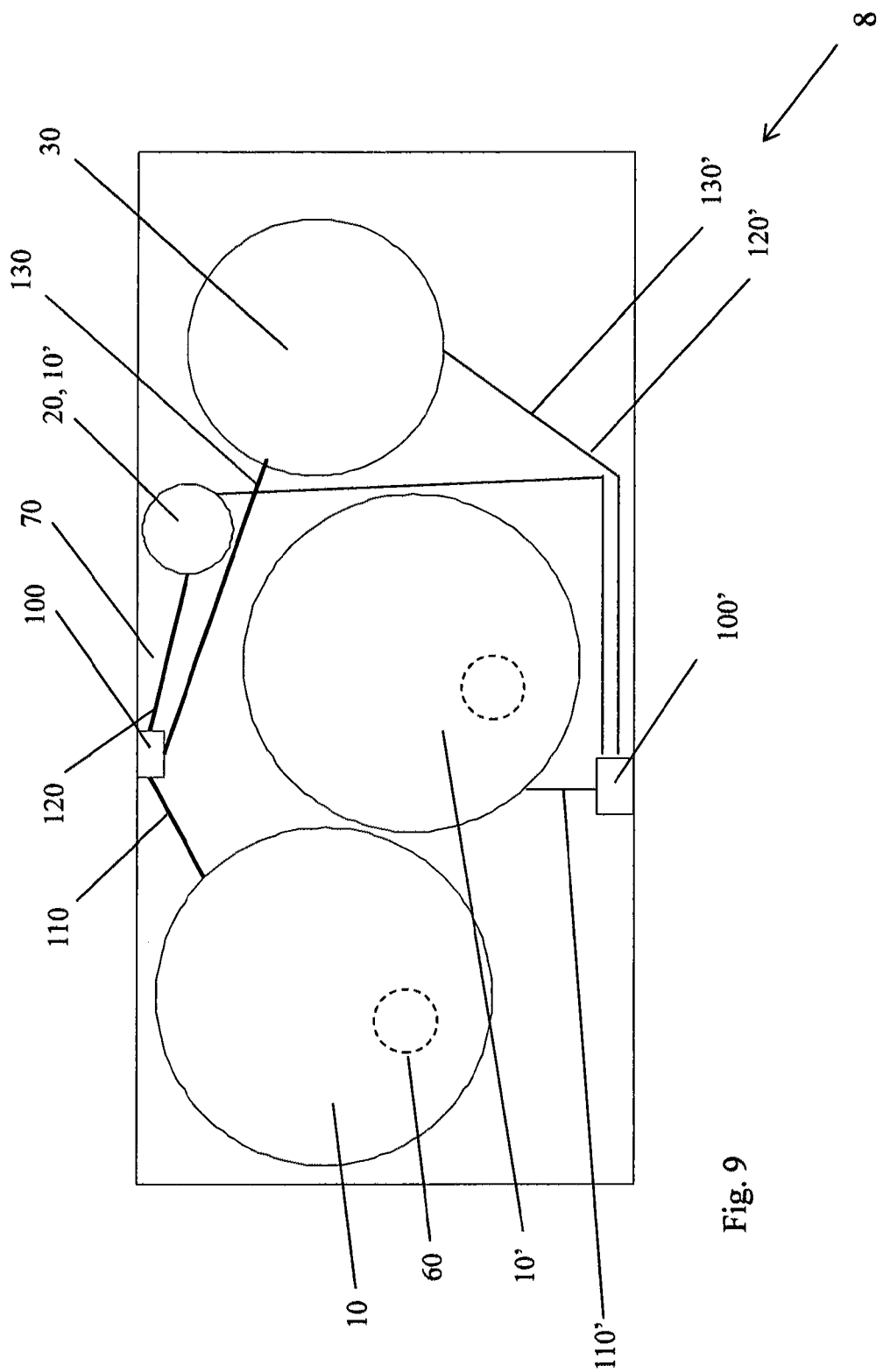
FIG. 9 is a schematic view of a third embodiment of the MEMS particle sorting system using a disposable cartridge with multiple sorting/separation stages.

FIG. 9 is another exemplary embodiment of a disposable cartridge 8 having multiple separation stages. In this embodiment, the two separation stages may operate on two different input reservoirs 10 and 10', and the sorted effluent collected in a single sort reservoir. In this embodiment, the sorting done by MEMS separation stages 100 and 100' may proceed in parallel, increasing the throughput of the device, allowing a single cartridge 8 to perform double the volume of sorting. Alternatively, the particle sorting system 1 into which this cartridge is inserted may be equipped with a secondary detection system and force-generating apparatus 1700, which would allow a two-fold increase in sort speed by accommodating the two independent, and simultaneously active sort stages 100 and 100'. In this embodiment, the passageways connecting the fluid reservoirs may empty into a single waste reservoir 30, and thus may be arranged in paths that require they go over and/or under another passageway.

Figure 10B:
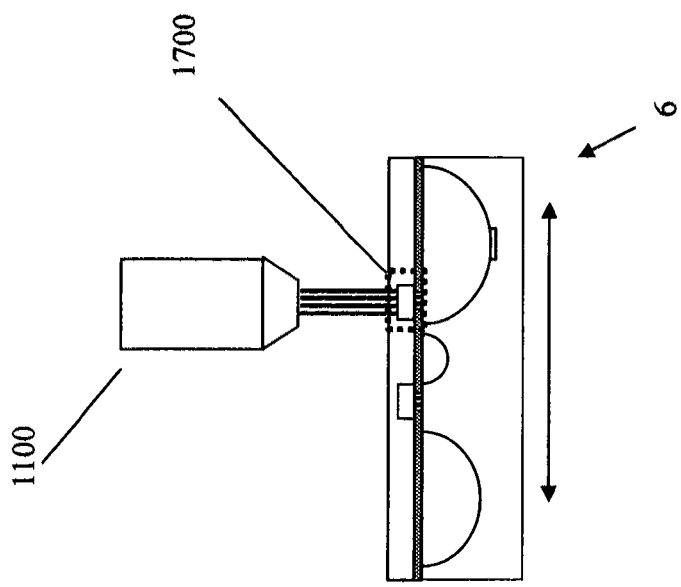
FIGS. 10a and 10b are schematic views of a embodiment of the MEMS particle sorting system using a disposable cartridge with multiple sorting/separation stage.
Figure 10A:
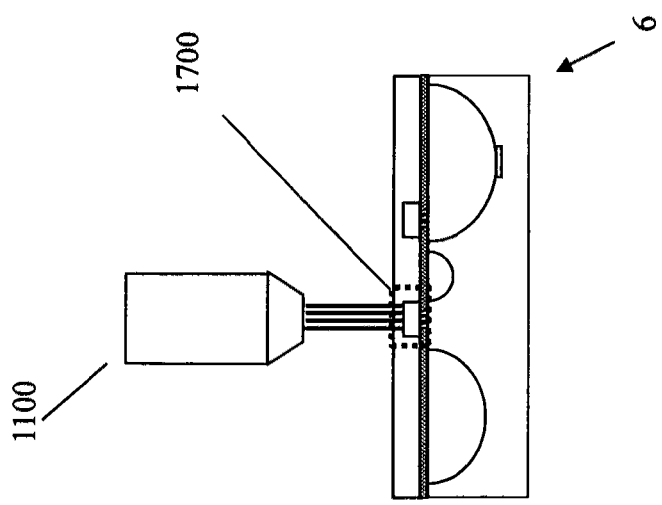

FIGS. 10a and 10b are simplified views of the disposable cartridge in the MEMS particle sorting system, showing operation with the disposable cartridge 6. In FIG. 10a, the input sample in sample reservoir 10 is sorted by the first separation stage 100 and the sorted effluent stored in reservoir 20. At this point, the cartridge 6 is positioned so that the first micromechanical actuator associated with separation stage 100 is positioned in the detection region of a laser-induced fluorescence optical detection system 1100. This system 1100 may include a laser source and a detector as was shown in FIG. 5. In FIG. 10b, the disposable cartridge 6 is translated to put the second micromechanical actuator in the detection region of a laser-induced fluorescence system. This position may also position the force-generating apparatus to operate on the second MEMS chip 100'. Simultaneously, the pumping system 90 may now be arranged to operate on the sort reservoir 20, 10' in order to apply fluid pressure to force the fluid through second MEMS chip 100'. The sorted effluent that was stored in reservoir 20 is thereby sent through the detection region and sorted a second time, and the now multiply-sorted sample may be stored in sort reservoir 200.

More broadly, the MEMS disposable cartridge use a plurality of particle manipulating structures, each performing a separate particle manipulating operation, but the operations all occurring within the fluid channels of the disposable cartridge. These particle manipulating structures may comprise additional devices installed in the disposable cartridge 5-8, or in the particle sorting system itself, or may be additional structures built into a single MEMS structure 100', but in all cases, the additional manipulation occurs within the disposable cartridge. Examples of such particle manipulating structures may include, for example, a laser, a set of electrostatic plates, a thermal source of heat, a movable lever, an input jet or channel, and a magnetic field-producing structure. ANYTHING ELSE? These structures may perform various particle manipulating operations, for example, at least one of the following: heating, pushing, irradiating, charging, tagging, changing the magnetic attributes of, damaging, destroying and altering a functionality of a target particle in the sample fluid. A secondary MEMS particle sorting stage may then separate the manipulated particle from others. Importantly, as these operations all take place while the target particles are enclosed in the disposable cartridge, the sample may remain sterile throughout the multiple operations.

In another embodiment of this general concept, the particle manipulating structure effectively may disable a sub-population of particles within the entire population of particles, and either the viable remaining population or the entire population, including the disabled particles, is collected in a sample reservoir after manipulation in the sterile disposable cartridge.

Figure 11:
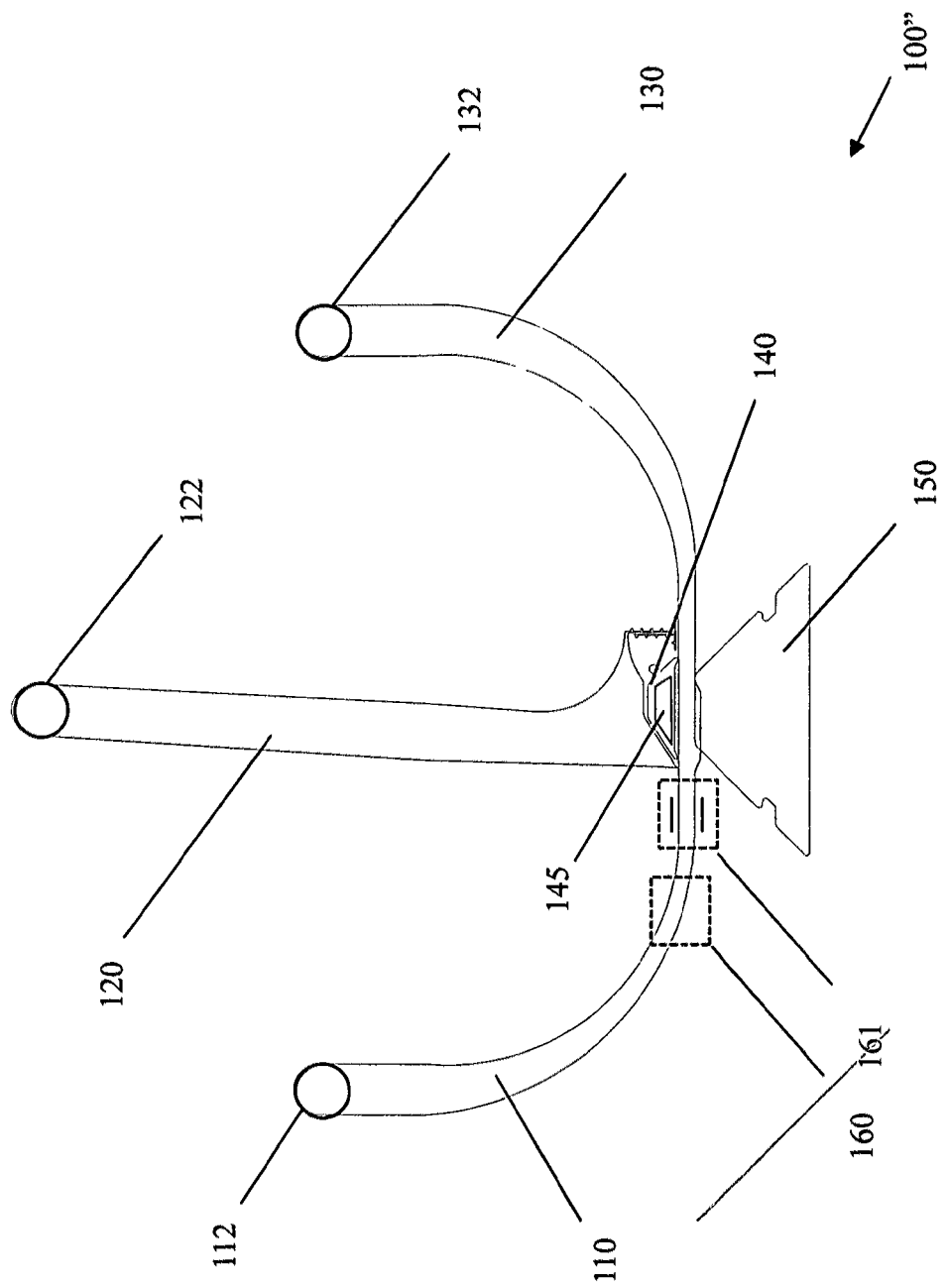
FIG. 11 is a schematic view of a fourth embodiment of the MEMS particle sorting actuator, wherein the device includes a secondary manipulation area wherein a target population of cells is manipulated.

FIG. 11 is a simplified schematic illustration of an embodiment of microfabricated MEMS device 100" which is consistent with the concept described above, of multiple manipulation stages in a single cartridge. In FIG. 11, a secondary region 161 exists within the sample passageway 110 of microfabricated MEMS device 100". This region may be used to incapacitate, damage or destroy a target cell identified in detection region 160. The mechanism may be thermal, radiative, mechanical, electronic, acoustic, or any other mechanism that interferes with the viability or function of a particle, and may be operated by a corresponding apparatus in the particle sorting system. In FIG. 11, a set of parallel electrostatic plates is shown, which may be energized to produce a strong electrostatic field in the region. This field may damage or destroy cells passing through it.

In another example, the same laser 1400 that was used to irradiate a tagged cell may be used to destroy that same cell in region 161 by turning up the output power of the laser 1400, and redirecting the spot focus of the beam as shown in FIG. 11. The technique may be used to inhibit or disable a targeted sub-population of cells. For example, the technique may be used to inhibit, damage or destroy all the male or female gametes in a system intended to separate the female gametes from the male gametes. Using this technique, although some of the non-desired gametes may be collected inadvertently during the sorting procedure, these cells are rendered non-viable or compromised by interaction with the strong laser field. Accordingly, the collected sample may contain active, viable cells only of the desired gender. The manipulated population may be collected in its entirety, as the targeted sub-population of cells has been effectively disabled, or the sample may be sorted to separate the remaining viable cells from the disabled or destroyed cells.

Figure 12:
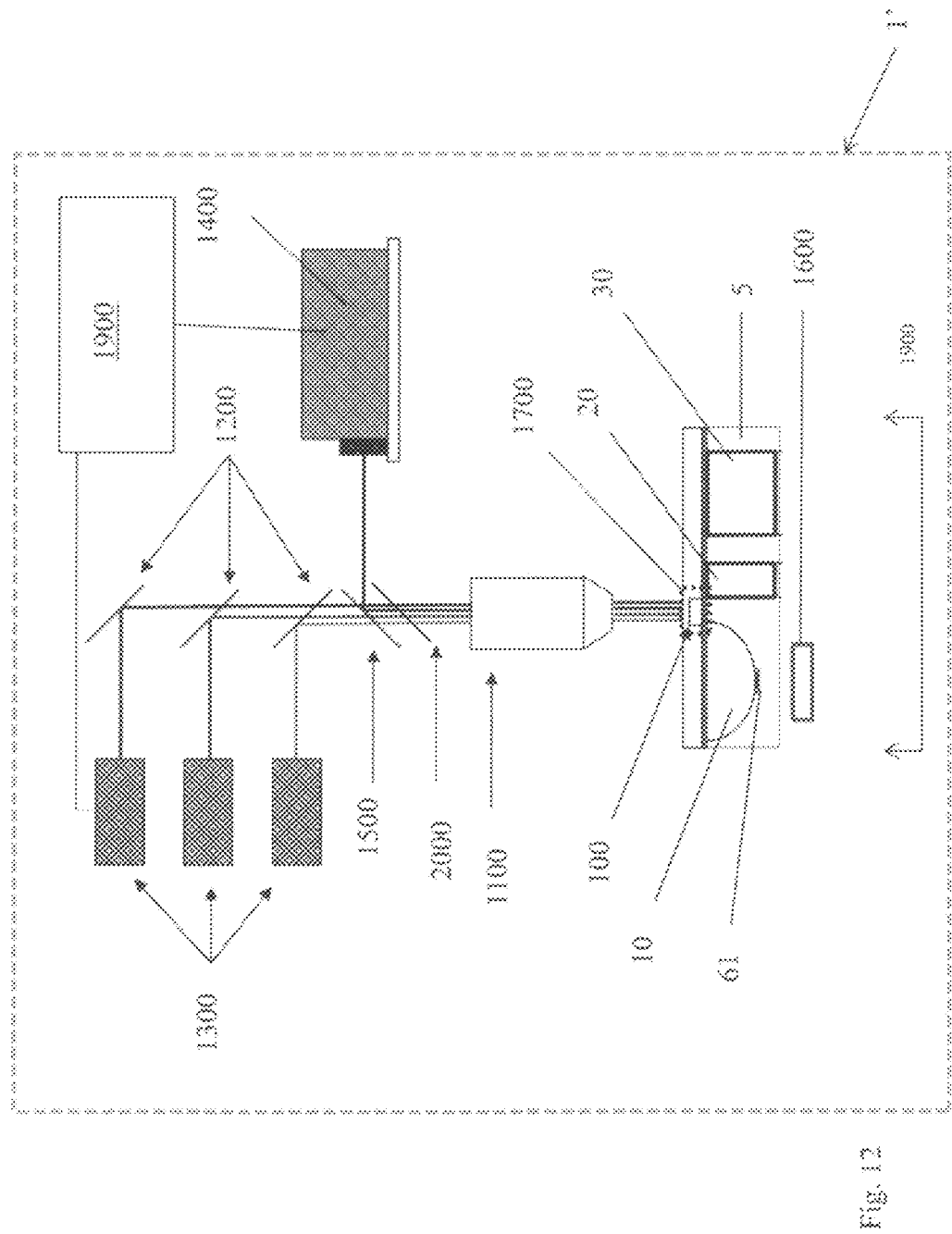
FIG. 12 is a schematic view of the disposable cartridge and MEMS particle sorting system, using the microfabricated MEMS particle sorting actuator of FIG. 11.

FIG. 12 is a simplified schematic illustration of a MEMS particle sorting system 1', similar to MEMS particle sorting system shown in FIG. 5. The system 1' shown in FIG. 12 is consistent with the multistage MEMS device 100, and system 1' includes an apparatus 2000 which uses the secondary region 161 shown in FIG. 11. In FIG. 12, an apparatus 2000 adjusts either the spot location or the beam energy of the laser source 1400 in the secondary region 161. As the time between detection and irradiation is short (that is, the path length between detection region 160 and secondary region 161 is short), the mechanism 2000 may be electronic in nature. For example, the mechanism 2000 may be a voltage supplying device that is applied across a variable attenuator, in order to reduce the laser intensity for interrogation, but allow full strength for disabling the target cell or particle. The mechanism may be combined with a high speed piezoelectric transducer to shift the beam spot laterally within the input channel 110. Alternatively, mechanism 2000 may be a voltage supplying device that supplies a voltage to the parallel electrostatic plates shown in FIG. 11.

It should be understood that the embodiments shown in FIGS. 6-12 are exemplary only, and are not meant to be exhaustive in the illustration of the ways in which the components of the multistage sorting cartridge may be arranged. Similarly, it should be understood that the mechanisms and structures illustrated in FIGS. 1-12 may be used to sort a wide variety of particles, including biological cells.

Figure 13:
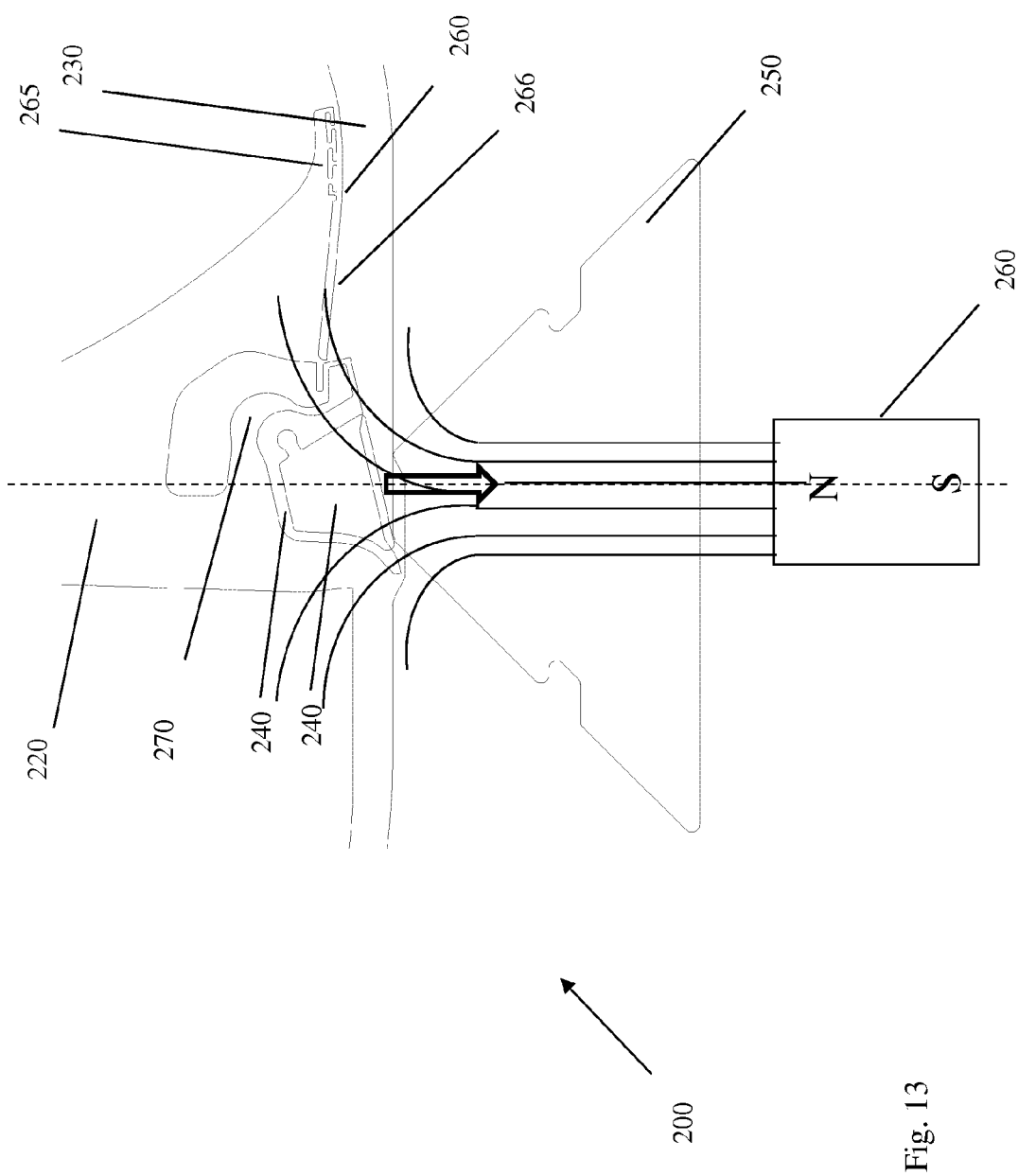
FIG. 13 is another embodiment of a MEMS actuator.

FIG. 13 shows another embodiment of a particle manipulation device with a movable structure 240. The motion of the movable structure 240 may be defined by its points of attachment to the substrate. In particular, if the motion of the movable structure 240 is substantially along an axis at any given point in time, the points of attachment may all be on one side of this axis. This axis is shown as the dotted vertical line in FIGS. 4 and 5. As a result, the motion of the movable structure tends to pivot about one side, thereby opening up an unobstructed pathway on the other side of the axis. Motion "substantially parallel to" or "substantially along an axis" should be understood to mean motion such that the angle between the vector of motion and the axis is less than 45 degrees at any given point in time. Because of this architecture, the movable structure is exceptionally small and has low inertia, and very low drag. But because the forces arising can be substantial, as described next, the movable structure can open and close the fluidic pathway exceedingly quickly, on the order of 25 usec. The motion can be predominantly linear or predominantly rotary, depending on how the movable structure 240 is attached to the substrate at the fixed points. An embodiment of each of these approaches is described below.

FIG. 13 is a detailed view of the micromechanical actuator in the sort position. In this figure, the flux source, or force generating portion 260 has been energized, such that flux is produced at its north pole. Since lines of magnetic flux find the lowest reluctance path to the south pole of the magnet, the lines are preferentially drawn into the permeable material, and focused in the vicinity of the tapered end of the magnetically permeable adjacent structure 250. They exit this structure 250 with high density and quickly disperse. The magnetically permeable portion 245 of the movable structure 240 is drawn toward this region of denser flux, pulling the magnet down and drawing the movable structure toward the adjacent magnetic structure 250. The magnetic force arising draws the movable structure from a first position (FIG. 4) in which the sort channel 220 is blocked and the default or waste channel 230 is open, to a second position wherein the sort channel 220 is open and the default channel is closed. This opens the fluidic pathway on the side of the movable structure (i.e. the sort channel 220) opposite the fixed points. A target particle, having been identified as such by in the detection region, is thereby diverted into the sort channel 220 by the action of energizing the electromagnet 260. The actuation force may be on the order of milliNewtons arising from a magnetomotive force (MMF) of about 25 ampere-turns in the force-generating apparatus 260. The total throw of the MEMS movable structure 240 may be about 25 microns, and this motion may take place in about 25 usec.

When the current to the coil of the force-generating apparatus 260 is discontinued, a spring force arising from flexible attachment 270 returns the movable structure 240 to its first position, closing the sort channel 220 and opening again the waste channel 230. The restoring force of this spring is designed to be on the order of about 100 N/m, so that the milliNewton actuation force is resisted by a comparable restoring force when the movable structure is deflected by 10-50 microns, in order to return the movable structure 240 to its first position in about 25 usec.

As described briefly above, the unique features of the multi-stage sorting concept may include the following distinguishing features compared to other known devices, such as those disclosed in the aforementioned '056, '972, '594 and '838 patents:

1. Sequentially located chips may allow sequential, or cascade sorting
2. $1^{st}$ stage output may become input for $2^{nd}$ stage, house stir bar for sample mixing
3. May include 'up and over' fluidic channel architecture, allowing effluent to pass to single waste chamber
4. May house a backflow preventer valve to allow pressurization during second sorting stage
5. May have sample ports for access to each fluidic chamber
6. May have viewable (via camera or microscope) chambers for $1^{st}$ and $2^{nd}$ stage sorted and un-sorter effluent
7. May include a secondary manipulation area, wherein particles are altered, damaged or destroyed prior to separation The multi-stage MEMS particle sorting device may be used in conjunction with a unique actuation mechanism, disclosed in co-pending U.S. Patent Application Serial No., assigned to the same assignee as the present invention.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A substantially sealed, disposable cartridge for a MEMS particle sorting system, comprising:
    a plurality of microfabricated particle manipulating structures formed on at least one substrate and installed in the substantially sealed, disposable cartridge, wherein the particle manipulating structure includes a movable structure formed in and from the layer of the substrate with a motion substantially in a plane, acted on by a magnetic force substantially in the same plane and wherein the movable structure simultaneously opens a first microfabricated fluidic channel which is in the plane and closes a second microfabricated fluidic channel also in the plane, and wherein the motion is substantially rotary, and the movable structure is attached to the substrate at one or more fixed points, and further comprising one or more flexible springs attached to the one or more fixed points, which return the movable structure to a first position when the force is removed;
    a quantity of biocompatible material with a plurality of fluid reservoirs disposed therein, with one or more fluidic passageways connecting the fluid reservoirs to the microfabricated particle sorting structures;
    wherein the plurality of particle manipulating structures are arranged to perform multiple manipulating operations on a sample fluid while the fluid is completely contained in the substantially sealed, disposable cartridge.

2. The substantially sealed, disposable cartridge of claim 1, wherein the plurality of particle manipulating structures are microfabricated particle sorting structures arranged within the substantially sealed, disposable cartridge so as to perform particle sorting operations sequentially on the sample fluid.

3. The substantially sealed, disposable cartridge of claim 1, wherein an effluent from a first manipulating operation is then used as input to another manipulating operation.

4. The substantially sealed, disposable cartridge of claim 1, further comprising:
    a flexible gasket covering a plurality of fluid reservoirs, wherein a plurality of holes formed in the gasket allows a fluid flow to between at least one of the reservoirs and at least one of the plurality of particle manipulating structures.

5. The substantially sealed, disposable particle sorting cartridge of claim 2,
    wherein the plurality of microfabricated particle sorting structures each has an associated sample passageway, sort passageway and waste passageway in fluid communication with the microfabricated particle sorting structure, and
    wherein the microfabricated particle sorting structures divert a target particle from the sample passageway to the sort passageway and blocks the waste passageway when the target particle is detected.

6. The substantially sealed, disposable cartridge of claim 1, further comprising:
    at least one vent formed in the biocompatible material which permits a gas to pass from at least one of the reservoirs to an environment external to the substantially sealed, disposable cartridge.

7. The substantially sealed, disposable cartridge of claim 4, further comprising:
    a lid affixed to the gasket to seal the gasket against the quantity of biocompatible material and against the substrate, and wherein the gasket is disposed against the quantity of biocompatible material on one side of the gasket, and the lid and substrate on another side of the gasket.

8. The substantially sealed, disposable cartridge of claim 5, wherein the plurality of microfabricated particle sorting structures, sample passageways, sort passageways and waste passageways are all in substantially the same plane.

9. The substantially sealed, disposable cartridge of claim 5, wherein an input septum is in fluid communication with the sample reservoir by a fluid channel linking the input septum with the sample reservoir.

10. The substantially sealed, disposable cartridge of claim 5, further comprising:
- a sample reservoir, a sort reservoir and a waste reservoir, each in fluid communication with the plurality of microfabricated particle sorting structures;
- at least one transparent viewing window disposed at the bottom of at least one of the sort reservoir and the waste reservoir.

11. The substantially sealed, disposable cartridge of claim 2, further comprising:
- at least one detection region upstream of at least one of the plurality of microfabricated particle sorting structures, wherein as the sample fluid flows through the detection region, a signal is obtained from the sample fluid which distinguishes a target particle from the other components of the sample fluid, wherein this signal is based on at least one of an electrical attribute, a hydrodynamic attribute, a magnetic attribute, mass, an optical attribute, a thermal attribute, and a mechanical attribute of the particle;
- and a secondary region upstream of the microfabricated particle sorting structure, wherein a targeted sub-population of particles is altered, damaged or destroyed.

12. The substantially sealed, disposable cartridge of claim 2, wherein:
- the microfabricated particle sorting structures each include a movable structure which pivots around at least one fixed point, wherein each of the fixed points is located on the same side of an axis of motion of the movable structure, and wherein the movable structure opens a sort channel to divert the target particle into the sort channel when the movable structure pivots about the at least one fixed point.

13. The substantially sealed, disposable cartridge of claim 10, wherein the sample reservoir has a curved floor forming the bottom of the sample reservoir; and wherein the sort reservoir and waste reservoirs each have a substantially rectangular cross section with a flat floor.

14. The substantially sealed, disposable cartridge of claim 9, further comprising:
- at least one transparent viewing window at the bottom of at least one of the sort reservoir and the waste reservoir, allowing the contents of at least one of the sort reservoir and the waste reservoir to be viewed from below the respective reservoirs.

15. The substantially sealed, disposable cartridge of claim 1, wherein at least one of the particle manipulating structures comprises at least one of a laser, a set of electrostatic plates, a thermal source of heat, a movable lever, an input jet or channel, and a magnetic field-producing structure.

16. The substantially sealed, disposable cartridge of claim 1, wherein at least one of the particle manipulating structures comprises at least one of a laser, a set of electrostatic plates, a thermal source of heat, a movable lever, an input jet or channel, a magnetic field-producing, radiative, mechanical, electronic, and an acoustic structure, wherein the particle manipulating structure effectively alters a sub-population of particles within the entire population of particles, and wherein the entire population is collected in a sample reservoir after manipulation in the sterile disposable cartridge.

17. A particle sorting system, comprising:
- the substantially sealed, disposable cartridge of claim 1; and
- at least one additional particle manipulating apparatus that performs at least one of the following: heating, pushing, irradiating, charging, tagging, damaging, destroying and altering a functionality of a target particle in the sample fluid, while in the sealed, disposable cartridge.

18. The substantially sealed, disposable cartridge of claim 17, wherein the at least one of the particle manipulating structures comprises a laser and an optical element which directs the laser beam into a secondary region, upstream of a particle sorting stage.

* * * * *

UNITED STATES PATENT AND TRADEMARK OFFICE
CERTIFICATE OF CORRECTION

PATENT NO. : 8,993,311 B2  
APPLICATION NO. : 13/506892  
DATED : March 31, 2015  
INVENTOR(S) : Foster et al.

Page 1 of 1

It is certified that error appears in the above-identified patent and that said Letters Patent is hereby corrected as shown below:

On the title page item (54) and in the specification, column 1, line 1, should read:

MULTI-STAGE CARTRIDGE FOR MEMS PARTICLE SORTING SYSTEM

Signed and Sealed this  
Thirtieth Day of June, 2015

Michelle K. Lee  
*Director of the United States Patent and Trademark Office*